(12) United States Patent
Ramella et al.

(10) Patent No.: US 8,622,986 B2
(45) Date of Patent: Jan. 7, 2014

(54) CONNECTOR FOR DISPOSABLE CONTAINER TO BE USED IN DIALYSIS MACHINES

(75) Inventors: Juan Miguel Angel Ramella, Buenos Aires (AR); Leonardo Franco Farace, Caba (AR)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 12/737,756

(22) PCT Filed: Aug. 4, 2009

(86) PCT No.: PCT/EP2009/005621
§ 371 (c)(1),
(2), (4) Date: Feb. 14, 2011

(87) PCT Pub. No.: WO2010/017906
PCT Pub. Date: Feb. 18, 2010

(65) Prior Publication Data
US 2011/0137280 A1    Jun. 9, 2011

(30) Foreign Application Priority Data

Aug. 13, 2008 (AR) ................ P080103526

(51) Int. Cl.
*A61M 5/32* (2006.01)
*A61B 19/00* (2006.01)
*B65D 39/00* (2006.01)

(52) U.S. Cl.
USPC ............ 604/416; 604/408; 604/410; 215/235

(58) Field of Classification Search
USPC ............................. 604/408, 410, 416; 215/235
See application file for complete search history.

(56) References Cited

U.S. PATENT DOCUMENTS

| 4,545,495 A | 10/1985 | Kinsley |
| 5,534,228 A * | 7/1996 | Wesseler ................ 422/541 |
| 7,137,654 B2 * | 11/2006 | Segal et al. ............ 285/330 |
| 7,828,786 B2 | 11/2010 | Ramella |
| 2003/0168120 A1 | 9/2003 | Brehm et al. |
| 2005/0096625 A1 | 5/2005 | Brandl et al. |
| 2008/0208159 A1 * | 8/2008 | Stanus et al. ............. 604/408 |

FOREIGN PATENT DOCUMENTS

| AR | 035471 A1 | 6/2004 |
| AR | 037133 A1 | 10/2004 |
| EP | 1 344 550 A1 | 9/2003 |
| JP | 2003-275299 | 9/2003 |
| WO | WO 99/06083 A1 | 2/1999 |
| WO | WO 2004/069307 | 8/2004 |

* cited by examiner

*Primary Examiner* — Tatyana Zalukaeva
*Assistant Examiner* — Andrew J Mensh
(74) *Attorney, Agent, or Firm* — Jacobson Holman PLLC

(57) ABSTRACT

The present invention relates to a connector for a replaceable container to be used in a medical machine, which is comprised by at least a body, the inner side of which is traversed by inlet and outlet tubes extending from within such container towards an outer side of the connector, wherein said tubes separately extend leading to two laterally spaced-apart apertures that are removably attachable to a mounting means and supplementary connection of said machine.

14 Claims, 5 Drawing Sheets

CONNECTOR FOR DISPOSABLE CONTAINER TO BE USED IN DIALYSIS MACHINES

This is a national stage of PCT/EP09/005621 filed Aug. 4, 2009 and published in English, which claims the priority of Argentina number P080103526 filed Aug. 13, 2008, hereby incorporated by reference.

FIELD OF THE INVENTION

Hemodialysis machines use one or several aqueous solution salt concentrates—such as, for example, a sodium bicarbonate solution—to purify blood in patients under dialysis treatment, thus working as a sort of artificial kidney. This concentrate can be derived by the machine from powdered or granular salt compounds that are provided in disposable, replaceable containers that can be of a bag type. In the standard process, water is provided by the machine to dissolve, e.g. the powdered sodium bicarbonate, the usable solution being concomitantly removed from the container through a separate tube.

The present invention relates to a connector that is disposed in the container and serves to attach the container to the dialysis machine, which connector is formed by the water inlet and solution outlet.

BACKGROUND OF THE INVENTION

Patent EP No 1,344,550 describes a connector that serves the same purpose, made of one piece with three tubes. The main tube is a central bore which completely traverses the member between its outer and inner sides (the latter being thus defined because it is within a tubular container once the connector is placed in the corresponding opening in such container), which is used to fill the container with soluble solid powdered or granular salts, whereby it has a greater diameter. The other two tubes are designed for water inflow and solution outflow, respectively, and they each have a length that is parallel to the central tube from the inner side of the connector to the vicinity of the outer side, wherefrom they outwardly diverge to extend in a parallel direction along a respective side wing or along the edge of the outer side leading to a cylindrical portion configured to be plugged into a dialysis machine. FIGS. 4 and 5 of such European Patent show the general features of a mounting console of the aforesaid dialysis machine model, wherein the side tubes are seen following paths forming more than one bend such that, for mold-designing purposes, if the member were made of plastic, the open side tubes could be molded on the outer side.

The pre-filling operation is typically carried out during the container manufacturing process itself and it can be followed by a sealing operation wherein a compliant sheet is welded onto the outer side of the connector to cover the mouth of the central tube, as can be seen in FIG. 2 of the aforementioned European Patent No. 1,344,550, to avoid both the loss of its contents and its contamination within the container. These procedures are performed in a sterile area. The same sheet also covers the side tubes that are molded with openings therein, as shown in FIG. 1 of such patent.

Patent AR No 37,133 refers to a connecting cap for a bi-compartment bag used with another hemodialysis machine. FIGS. 3; 4, and 5 of such patent AR No 37,133 show a connector having two inlet and outlet tubes, which is made of an assembly of two sealed and nested members. One member is of annular shape and it is incorporated into the replaceable bag in such a manner that on its inner side, each tube is in fluid communication with a separate compartment. The second, central member is not placed within the annular member until just after the bag has been pre-filled with the powdery product through the larger diameter central tube. The central member is formed with a disk sealing the central tube once it has been snapped into the annular member, thus forming a connector to attach the bag to the dialysis machine when the latter opens such disk as a valve to let the water in and dissolve the product, with the machine removing the resulting solution via the side tube.

Finally, FIGS. 2 and 3 of Published Patent Application AR No 35,471 show a two-piece molded connector having ribs to allow for its assembly.

SUMMARY OF THE INVENTION

An object of the present invention is to develop another connector to be used on this type of replaceable container as described in AR No 35,471.

Another object of this invention is to eliminate the opening-sealing procedure on the outer side of the connector by means of a welded sheet or film, as is done in the aforementioned European Patent. A further object is a connector structure that is provided with a novel sealing system that is effective for one- or two-compartment disposable containers.

The further problem solved by the invention is that of achieving a sealing of the open channels or grooves formed by the tubes around the outer side of the connector wings, in a safer and more cost-efficient manner.

The problems are solved by a connector for a replaceable container having walls, the container having a member with an opening in one of the walls, the container to be used in a medical machine. The connector is comprised of at least a body, the inner side of which is traversed by inlet and outlet tubes extending from a central member within such container when the connector is attached to the container by joining the central member to the member with the opening, towards an outer side of the connector. The tubes separately extend leading to two laterally spaced-apart apertures that are removably attachable to a mounting element and supplementary connection of the machine.

The present invention further includes a connector as described in the previous paragraph in combination with a replaceable, disposable container closed by the connector.

The present invention further includes a method of making a connector for a replaceable container having walls, the container having a member with an opening in one of the walls, the container to be used in a medical machine as described above. The connector includes at least a body, the inner side of which is traversed by inlet and outlet tubes extending from a central member within such container when the connector is attached to the container by joining the central member to the member with the opening, towards an outer side of the connector. The tubes separately extend leading to two laterally spaced-apart apertures that are removably attachable to a mounting element and supplementary connection of the machine. The method comprises molding the body having the inlet and outlet tubes traversing the inside thereof from the inner side of the container to an outer side of the connector, the tubes separately extending parallel or along the edge of the outer side of the connector leading to two removably attachable apertures. The body is molded with openings on the outer side disclosing the open portions in both tubes and has a cap that conforms to the openings. The cap is affixed to the body by flexible, hinged or frangible linkages, such that the cap can fold around such linkages until it covers the exposed portions of the tubes.

Still further, the present invention includes a method of making a replaceable device containing a powdered, granular or similar matter to be attached to a medical machine for preparing medical solutions, in particular dialysis solutions. The method includes providing a device comprising two members, with one of the two members being a container provided with a member having an opening, the other member being a connector. The connector includes at least a body, the inner side of which is traversed by inlet and outlet tubes extending from a central member within such container when the connector is attached to the container by joining the central member to the member with the opening, towards an outer side of the connector. The tubes separately extend leading to two laterally spaced-apart apertures that are removably attachable to a mounting element and supplementary connection of the machine. The method further includes filling the container by introducing into the container a solid matter through the opening, and fitting the connector within the opening of the member of the container, such the connector and the container form a sealing fit.

These and other benefits, objects and solutions, which will become apparent from the following description, are in one embodiment achieved by shaping a connector having a cap attached to the connector body itself by means of compliant, hinged, or frangible linkages. In a further operation, the cap is folded around the outer side and sealingly closed to block the tube openings on the side wings thereof.

In a preferred embodiment, the connector comprises an member, preferably an annular member, lodged in the bag opening and that is configured as disclosed in Patent Application AR 35,471, through which the solid product pre-filling operation is carried out, and a central member that makes up a nozzle with the essential features of the connector as listed in the previous paragraphs.

The disclosures of the patent applications AR 35,471 and EP 1 344 550 A1 are incorporated in the present application by reference.

BRIEF DESCRIPTION OF THE DRAWINGS

For a ready understanding of the present invention and the manner it can be put in practice, a detailed description of a preferred embodiment of the invention is shown below, with reference to the exemplary drawings appended thereto, that are intended to be illustrative, and not limiting of the invention, and the components of which will be selected by the skilled person from various equivalents without departing from the principles of the invention. In the appended drawings it can be seen that.

DETAILED DESCRIPTION OF THE PREFERRED EMBODIMENT

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Figure 1:
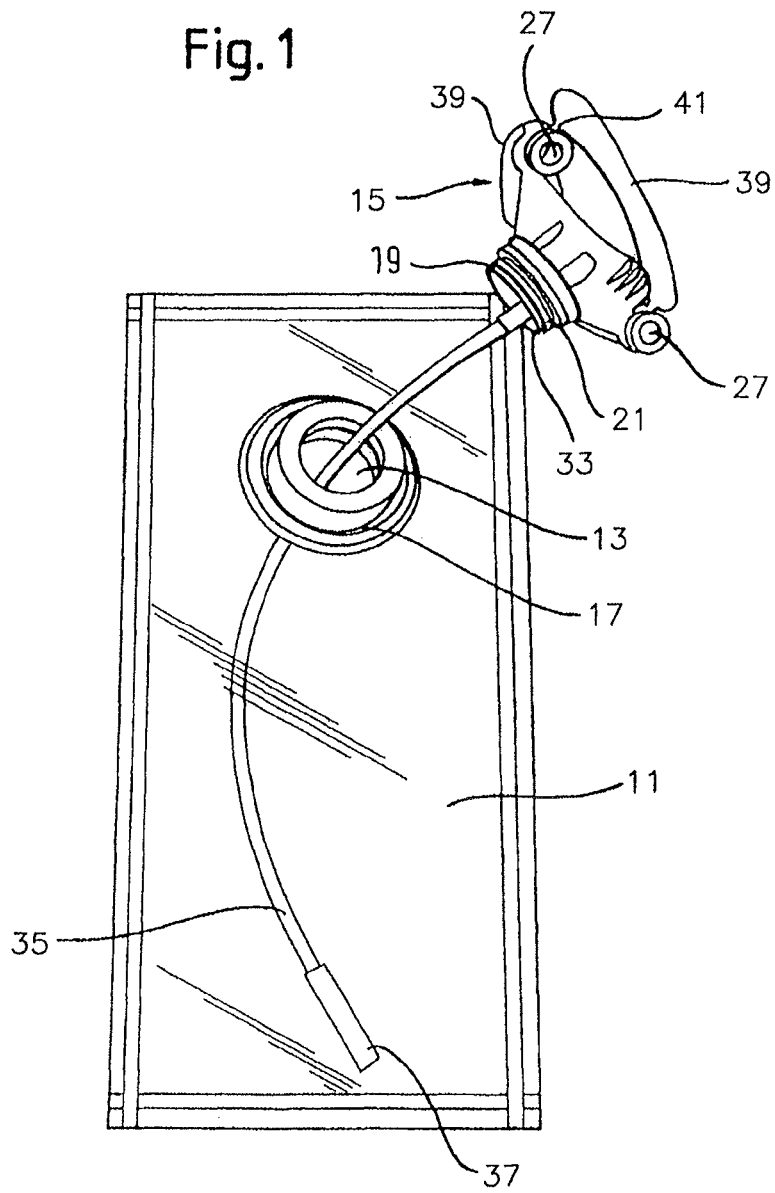
FIG. 1 is an exploded perspective view of a single-compartment disposable dialysis bag provided with a connector according to a preferred embodiment of the present invention.

With reference to FIG. 1, it is first shown an elongated single-compartment bag 11 made of two wall sheets having an opening 13 in one of the wall sheets, and a connector 15 that is shown unattached for illustration purposes. In order to place the connector member 15 in the bag, an ancillary member 17 which in this embodiment is of annular shape is positioned at the rim of the opening 13, which annular member is capable of centrally receiving the connector body 15 within its throat or opening 13, thus forming a sealing fit.

Figure 2:
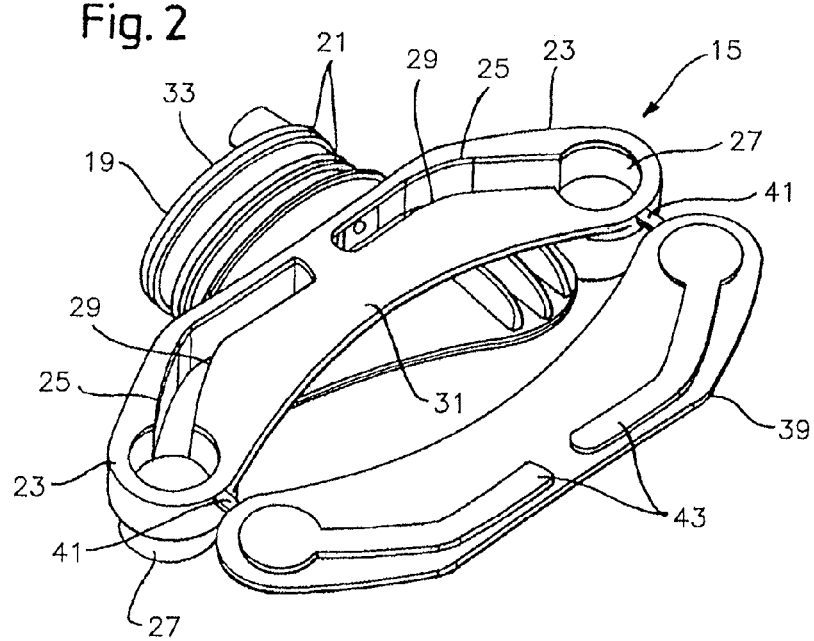
FIG. 2 is top perspective view of the connector shown in FIG. 1, with the collapsible cap initially open to expose the respective solvent and solution inlet and outlet ports.
Figure 3:
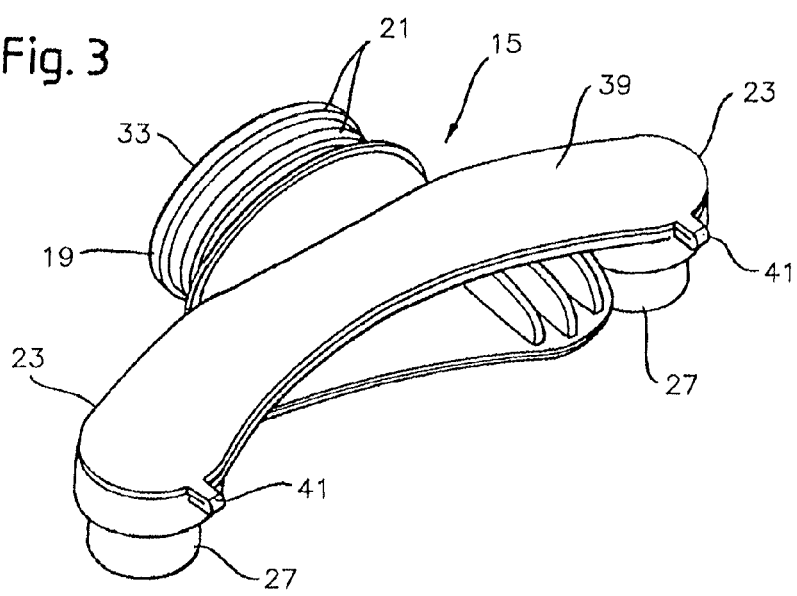
FIG. 3 is a perspective view, analogous to FIG. 2, but wherein the connector is shown with the collapsible cap closed, such that the inlet and outlet ports in all the extensions contiguous to the outer side of the piece are sealed.

As shown in FIG. 2, the member 15 comprises a central body 19 having annular ribs 21, which allow for a firm hold within the opening 13 of the annular member 17, and two wing-like lateral extensions 23 within which tubes or conduits 25 extend to respectively inject water and remove the solution therethrough. These conduits 25 extend from corresponding apertures 27 in the wing ends 23, that are configured to allow the attachment and connection to a dialysis machine (not shown), having some lengths that form channels 29 that are open on one end on the outer or rear side 31 of the member, then leading into the inner side 33 of the connector, wherein the solution outlet tube has an extremity for the attachment of a suction tube 35, the terminal edge of which ends in a filter 37 such that, in use, the latter is lodged at the bottom of the bag 11, at the opposite end of the opening 13. Similarly the inlet tube to inject the water can have a filter element directly at its end in the central body 19. The filter element can be made by various manufacturing techniques. In one embodiment the orifice of the inlet tube is covered by a non-woven welded sheet which is welded or glued to the central body. The inlet orifice may also have a small extremity pointing into the container and having an enlarged cross-section compared with the outlet tube.

For brevity purposes, any further details on the conventional aspects of the disclosure so far are omitted, since they are known from the aforementioned patents. The permanent bond between the annular member and the sheet material the bag 11 is made of, as well as the snap fitting thereto of the central member or the actual nozzle 15, may have the same characteristics as shown in the above Publication AR No 35,471.

In accordance with one aspect of the invention, the connector member 15 is molded with a cap 39 attached thereto by two linking flexible strips 41. Such cap 39 has the same transversally elongated configuration as the aforementioned rear side 31 of the wings 23 in the connector 15, together with internal protuberances 43 replicating the open portions 29 of the tubes. Thus, it is easy to understand that, when the cap 39 is folded over the outer side 31 of the connector 15, thus folding the strips 41 which attach it to the ends of wings 23, protuberances 43 snap fit within the open channels 29 far enough to seal them, the sealing being guaranteed by ultrasound or laser welding.

In the illustrated example, wings 23 have an 87.3 mm span to accommodate a 78.0 mm length between the central points of the mounting apertures and connection 27. The open channels 29 have a 4.1 mm width, whereas the cap 39 has a 1.0 mm thickness, just like protuberances 43 on the inner side of the cap 39. Strips 41 attaching the cap onto the body 15 of the connector are 3.0 mm long, 2.0 mm wide and 0.8 mm thick.

Figure 4:
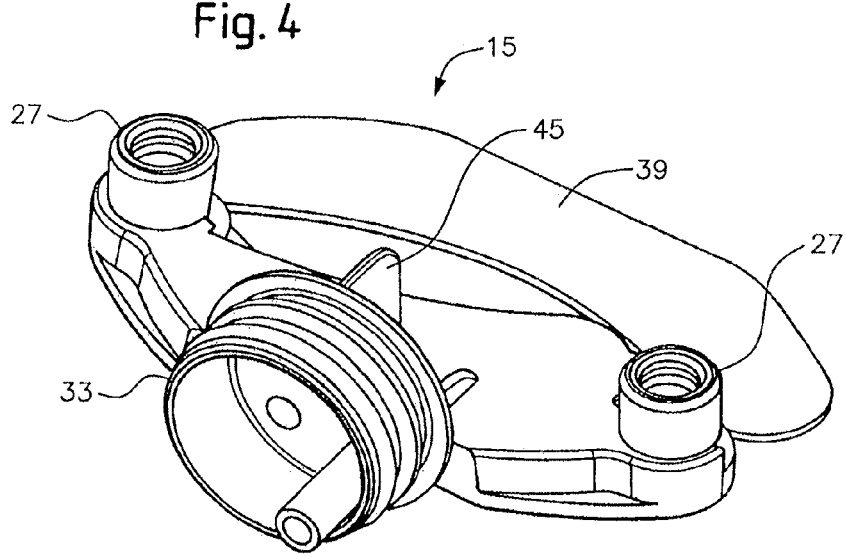
FIG. 4 is a bottom front perspective view of the connector shown in FIG. 1 as molded.
Figure 5:
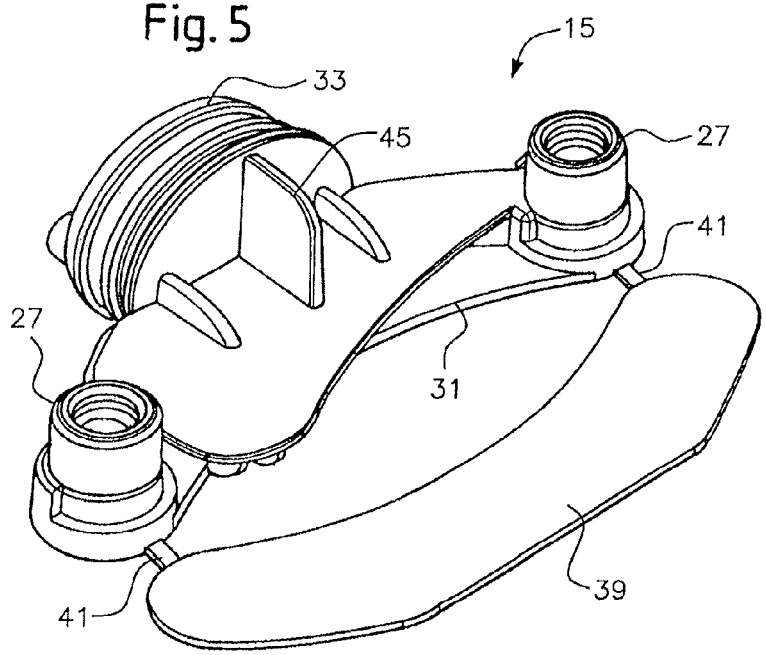
FIG. 5 is a bottom rear perspective view of the connector shown in FIG. 4.
Figure 6:
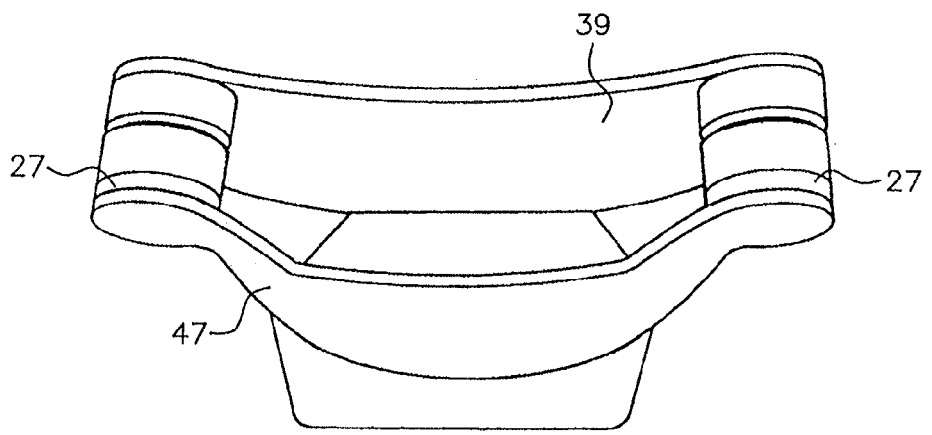
FIG. 6 is a bottom perspective view of the connector shown in FIG. 2 with its connection ports now sealed.
Figure 7:
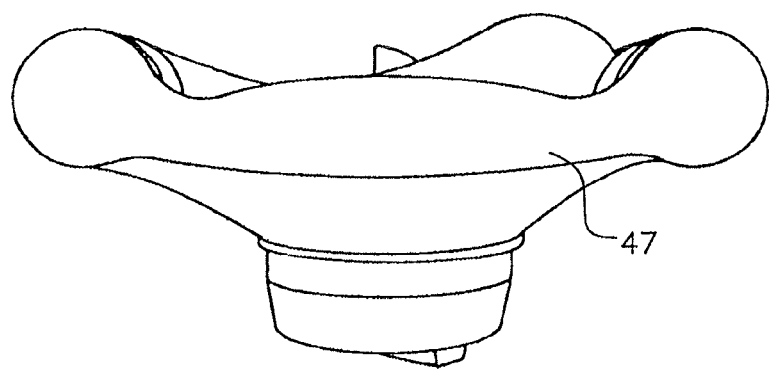
FIG. 7 is a rear perspective view of the connector shown in FIG. 6.
Figure 8:
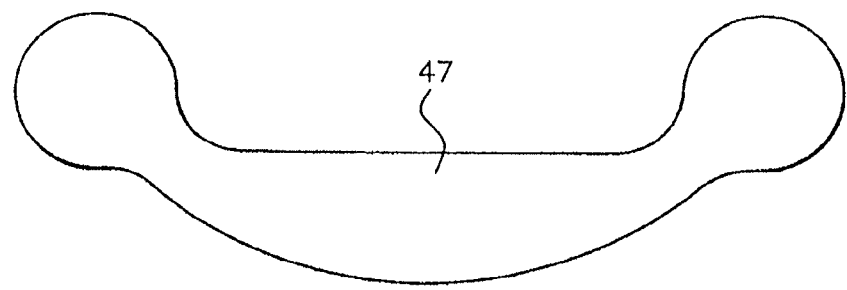
FIG. 8 is a view of the member that is sealingly affixed to the connector as shown in FIGS. 6 and 7.

FIG. 4 shows the apertures 27 that the channels 29 of the connector 15 lead into, and FIG. 5 shows a reinforcing structure 45 that serves to stiffen the said member. Once the central piece 15 of the connector with the cap 39 already welded onto it, as disclosed above, and the bag 11 with the annular member 17 have been made, the powdered product is filled into the bag 11. The member 15 of the actual connector is then placed on the annular member 17, by first introducing the suction tube 35, which serves as an extension of the solution outlet, such that the filter 37 reaches the bottom of the bag 11. Both apertures 27 are sealed as shown in FIGS. 6 and 7 by means of a polyester-coated sheet 47 as shown in FIG. 8, which is bonded by a peel-off hot melt, and then the filled and sealed device containing the substance to be dissolved is ready to be shipped to a point of use, i.e. a hospital, clinic or dialysis center. It is seen that the annular member 17 serves two purposes: as an inlet port for the solid matter to be dissolved and as a sealing mounting and retention member on the central member of connector 15 having the characteristics of a finished plug.

When it is time for use, the device is promptly attached to a dialysis machine, after the peel-off sheet 47 has been lifted from apertures 27, and plugged into the mounting console of the machine, after which the latter will pump pure or distilled water via one of the tubes 25 in order to dissolve the solid matter. After being contacted by water, such solid matter forms a solution with the solid contents that is capable of passing through sieve 37 such that it can be sucked by tube 35 and carried through the outlet tube 21 into the machine for the purifying treatment of the blood taken from the patient to be detoxified and returned by extracorporeal circulation in the case of hemodialysis. When the product in the device bag has been depleted, the connecting apertures 27 are unplugged and the device is disposed of or replaced to perform another treatment with a new device.

It will be apparent that various modifications and additions could be introduced into the embodiment disclosed herein, as long as they are consistent with the spirit and scope of the present invention. For instance, while the invention has been described regarding a replaceable device suitable for a hemodialysis machine, it should be apparent that the solution provided could eventually be used in other medical application with analogous problems to solve such as a peritoneal dialysis machine. It should also be apparent that while the described embodiment uses a bag, the concept of the invention is applicable to containers in general, independent of the flexibility of the walls of the container.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A connector for a replaceable container having walls, the container having a member with an opening in one of the walls, the container to be used in a medical machine, said connector comprising at least a body, the inner side of said body being traversed by inlet and outlet tubes extending from a central member within the container when the connector is attached to the container by joining the central member to the member with the opening, towards an outer side of the connector, said tubes separately extending and leading to two laterally spaced-apart apertures that are removably attachable to a mounting element and supplementary connection of the machine, the outer side of said connector including an integrally molded cap that is initially open such that the cap exposes a portion of each of said tubes which extend parallel, or along the edge of said outer side of the connector, said cap being bonded to the connector body by flexible, hinged or frangible linkages in such a manner that the cap is initially capable of folding around the linkages until the cap covers the initially exposed portions of the tubes, said cap being a planar member having an inner side that is provided with protuberances that correspond to open lengths of said tubes to allow the cap to fit into and seal the tubes, the sealing being made permanent by ultrasound or laser welding thereof.

2. The connector according to claim 1, wherein said body, cap and linkages are molded in one piece of a synthetic material.

3. The connector according to claim 1, wherein said linkages include two spaced-apart flexible strips that attach a same edge of the cap to a corresponding edge of the connector body.

4. The connector according to claim 1, wherein said cap has an elongated shape and said linkages are affixed to a long edge of the cap.

5. The connector according to claim 1, wherein said body and cap are molded as separate members of a synthetic material.

6. The connector according to claim 1, wherein said two removable attachable apertures are sealed by a peel-off means.

7. The connector according to claim 1, wherein the member with the opening and the central member have an annular shape.

8. The connector according to claim 1, wherein the central member has annular ribs to snap fit on the member with the opening.

9. The connector according to claim 1, in combination with a replaceable, disposable container, said container being closed by said connector.

10. The connector and the replaceable, disposable container according to claim 9, wherein said container contains powdered or granular compounds usable for making dialysis solutions.

11. A method of making a connector comprising steps of:
providing a container having a member with an opening in one of the walls, the container to be used in a medical machine,
providing a connector having a body and two laterally spaced-apart apertures that are removably attachable to a mounting element;
providing an integrally molded cap on an outer side of said connector, that is initially open such that the cap exposes a portion of each of said tubes which extend parallel, or along the edge of said outer side of the connector, said cap being bonded to the connector body by flexible, hinged or frangible linkages in such a manner that the cap is initially capable of folding around the linkages until the cap covers the initially exposed portions of the tubes, said cap being a planar member having an inner side that is provided with protuberances that correspond to open lengths of said tubes to allow the cap to fit into and seal the tubes, the sealing being made permanent by ultrasound or laser welding thereof;

molding the body to have inlet and outlet tubes traversing an inside thereof from an inner side of said container to an outer side of the connector, said tubes separately extending parallel or along an edge of said outer side of the connector leading to two removably attachable apertures;

said step of molding including forming openings on said connector outer side disclosing exposed portions in both tubes;

said cap conforming to said openings and being affixed to said body by flexible, hinged or frangible linkages such that said cap can fold around such linkages until said cap covers the exposed portions of said tubes, said cap being initially open such that the cap discloses the exposed portion of each of said tubes, said cap being a planar member having an inner side that is provided with protuberances that correspond to the exposed portions of said tubes to allow the cap to fit into and seal the tubes;

fitting the cap into the tubes to seal the tubes; and permanently sealing the tubes by ultrasound or laser welding the cap thereto.

12. The method of making a connector according to claim 11, wherein said cap is molded as a separate member.

13. The method of making a connector according to claim 11, wherein said two apertures are sealed by a peel-off sheet.

14. A method of making a replaceable device containing a powdered or granular material to be attached to a medical machine for preparing medical solutions, said method comprising steps of:

a) providing a device having two members, one of said members being a container provided with a member having an opening, the other member being a connector, said connector including at least a body, the inner side of said body being traversed by inlet and outlet tubes extending from a central member within the container when the connector is attached to the container by joining the central member to the member with the opening, towards an outer side of the connector, said tubes separately extending and leading to two laterally spaced-apart apertures that are removably attachable to a mounting element and supplementary connection of the machine, the outer side of said connector including a cap that is initially open such that the cap exposes a portion of each of said tubes which extend parallel, or along the edge of said outer side of the connector, said cap being bonded to the connector body by flexible, hinged or frangible linkages in such a manner that the cap is initially capable of folding around the linkages until the cap covers the initially exposed portions of the tubes, said cap being a planar member having an inner side that is provided with protuberances that correspond to open lengths of said tubes to allow the cap to fit into and seal the tubes;

b) filling the container by introducing solid matter into the container through the opening, c) fitting the connector within the opening of the member of the container, such that they form a sealing fit; and d) making the sealing fit permanent by ultrasound or laser welding thereof.

* * * * *

UNITED STATES PATENT AND TRADEMARK OFFICE
CERTIFICATE OF CORRECTION

| | |
|---|---|
| PATENT NO. | : 8,622,986 B2 |
| APPLICATION NO. | : 12/737756 |
| DATED | : January 7, 2014 |
| INVENTOR(S) | : Ramella et al. |

It is certified that error appears in the above-identified patent and that said Letters Patent is hereby corrected as shown below:

In the claims:

Claim 14, column 8, line 11, change "a" to --an integrally molded--.

Signed and Sealed this
Fifteenth Day of April, 2014

Michelle K. Lee
*Deputy Director of the United States Patent and Trademark Office*